United States Patent [19]

Bell

[11] 4,279,156

[45] Jul. 21, 1981

[54] PARTICLE COLLECTOR AND FRACTIONATOR

[75] Inventor: John P. Bell, Raleigh, N.C.

[73] Assignee: The United States of America as represented by the Administrator of the United States Environmental Protection Agency, Washington, D.C.

[21] Appl. No.: 89,011

[22] Filed: Nov. 29, 1979

[51] Int. Cl.³ .................................... G01N 1/24

[52] U.S. Cl. .................................... 73/863.22

[58] Field of Search .................................... 73/28, 421.5 R

[56] References Cited

U.S. PATENT DOCUMENTS

| | | | |
|---|---|---|---|
| 2,538,116 | 1/1951 | May | 73/28 |
| 3,092,583 | 6/1963 | Wolff et al. | 73/28 |
| 3,741,001 | 6/1973 | Fletcher | 73/28 |

*Primary Examiner*—S. Clement Swisher

[57] ABSTRACT

A particle collector and fractionator having a 360°, omnidirectional gas slit is disclosed herein. The collector and fractionator generally comprise a top and a bottom fractionating member, each of which has a set of concentric corrugations which are complementary to the other set. The collector also includes at least one spacer bracket for mounting and spacing the concentric corrugations of the top fractionating member over the concentric corrugations of the bottom member in complementary relationship, and forming an annular, concentrically corrugated gas flow path therebetween which is circumscribed by a 360° gas slit. Particles are collected and fractionated in the valley portions of the concentric corrugations of the top and bottom members whenever particle laden gas flows from any direction into the concentrically corrugated gas flow path, and out through a centrally disposed gas withdrawal means in the bottom fractionating member. The minimum aerodynamic size of the particles collected and fractionated may be selected by adjusting the spacer brackets to vary the cross sectional area of the gas flow path, which in turn increases or decreases the velocity of a stream of particle laden gas flowing through the path.

12 Claims, 4 Drawing Figures

PARTICLE COLLECTOR AND FRACTIONATOR

BACKGROUND OF THE INVENTION

This invention relates to particle collectors and fractionators for both collecting and fractionating particles from a stream of gas. While the instant invention may be used in any application requiring the separation of particulate matter from a gaseous medium, the invention is particularly well suited for separating and fractionating fine particles of pollutants from the ambient atmosphere incident to air sampling tests, as will become apparent hereafter.

Particle collection and fractionating devices are well known in the prior art. Examples of such devices appear in U.S. Pat. Nos. 2,947,164, 3,693,457, 3,823,602, 3,922,905 and 3,938,366.

Ideally, a particle collector and fractionator should be easy to clean and simple in construction, but nonetheless capable of accurately fractionating and effectively collecting a group of gas suspended particles into a large number of discrete categories of aerodynamic diameters. Moreover, when the collector is being used to collect particles of pollutants from the ambient atmosphere, the accuracy of the particle density measurements should not be affected by winds or other forms of air currents. Finally, such a collector should be convenient and simple to operate either by itself, or in conjunction with particle filters or other forms of conventional particle collecting and sampling equipment.

However, none of the particle collectors developed thus far in the prior art appears to possess all of the aforementioned desired features.

For example, while the particle collection and fractionating device disclosed in U.S. Pat. No. 3,823,602 is relatively simple in construction, this device must be inconveniently rotated by an electric motor or other means in order to collect and fractionate particle suspended in a gaseous medium. Furthermore, instead of fractionating the particles into discrete categories of different aerodynamic diameters, this device produces a continuous smear of particles of ever increasing aerodynamic diameters along a single collector strip. Additionally, the particle density measurements of this device are likely to be affected by winds or air currents since this device samples the air from only a single port, which may or may not be properly oriented with respect to wind direction to capture an air sample truly representative of the density of particle pollutants in the ambient atmosphere.

While the particle collection and fractionating device disclosed in U.S. Pat. No. 3,922,905 is both relatively simple in construction and easy to use, it is capable of fractionating the particles into only two categories of aerodynamic size. Moreover, since it samples the air from only a single plane surface, the accuracy particle density measurements of this device are also likely to be affected by the proper or improper orientation of this surface with respect to wind and air currents.

Finally, while the particle collection and fractionating devices disclosed in U.S. Pat. Nos. 2,947,164, 3,693,457 and 3,938,366 are each capable of fractionating the particles into a wide variety of size-categories, each of these devices is relatively complicated in structure, and consequently complicated to disassemble and clean.

Clearly, the foregoing prior art examples illustrate the need for a particle collection and fractionating device which is easy to clean, simple in construction, easy and convenient to use, capable of effectively separating the particles into a large number of aerodynamic size categories, and whose accuracy is completed unaffected by winds or other air currents.

SUMMARY OF THE INVENTION

The invention concerns a particle collector and fractionator which generally comprises a top and bottom fractionating member, each having a set of concentric corrugations which is complementary in shape to the other set, and a spacing bracket for spacing the corrugations of the top member over the corrugations of the bottom member in complementary relationship such that a concentrically corrugated gas flow path is formed between them. This gas flow path terminates around the adjacent edges of the spaced apart top and bottom fractionating members in a 360° omnidirectional gas slit. The invention also includes a gas withdrawal means for withdrawing particle laden gas from the center of the gas flow path, which may include a gas port centrally located in the concentric corrugations of either the top or bottom fractionating members which is fluidly connected to a source of negative pressure.

When a stream of particle laden gas enters the omnidirectional gas slit and flows through the gas flow path defined between the complementary corrugations of the top and bottom fractionating members, particles in the gas stream are impacted on and collected in the valley portions of the corrugations as they attempt to negotiate the turns from the narrow, high pressure flow paths defined parallel legs of the corrugations around the wider, low pressure flow paths defined between the complementary peak and valley portions of the corrugations.

The minimum aerodynamic size of the particles collected in the valley portions of the corrugations may be selected by adjusting the spacer brackets to vary the radial velocity of the gas stream flowing through the flow path by increasing or decreasing the cross sectional area of the disc shaped flow path between the complementary concentric corrugations. When the invention is constructed so that the annular cross sectional areas of the gas flow path between the parallel surfaces of the concentric corrugations of the fractionating members is constant from the outermost to the centermost corrugation, the radial velocity of the gas stream remains substantially constant at each point as the stream converges toward the centrally disposed gas port. Consequently, particles of approximately the same minimum aerodynamic size are collected at each valley portion of the concentric corrugations. However, when the invention is constructed so that the annular cross sectional area of the gas flow path between the corrugations becomes progressively smaller from the outermost to the centermost corrugation, the speed of the gas increases at each successive annular cross section. Consequently, particles of progressively smaller aerodynamic sizes are collected in each successive valley portion of the corrugation.

The particle collector and fractionator of the invention is thus simple in construction, easy to use, and may be easily cleaned by simply detaching the spacer brackets and separating and cleaning the two fractionating members. As the invention contemplates the use of six or more sets of complementary concentric corrugations, it is easily capable of fractionating particles in a stream of gas into six or more discrete categories. Furthermore, the adjustability of the spacer brackets allows all six of the fractionating stages defined by the six sets of corrugations to be adjusted simultaneously. Finally, the use of a 360°, omnidirectional gas slit provides a particle collector and fractionator whose particle density measurements are essentially unaffected by the direction of winds or air currents.

BRIEF DESCRIPTION OF THE SEVERAL DRAWINGS

DETAILED DESCRIPTION OF THE PREFERRED EMBODIMENTS

Figure 1:
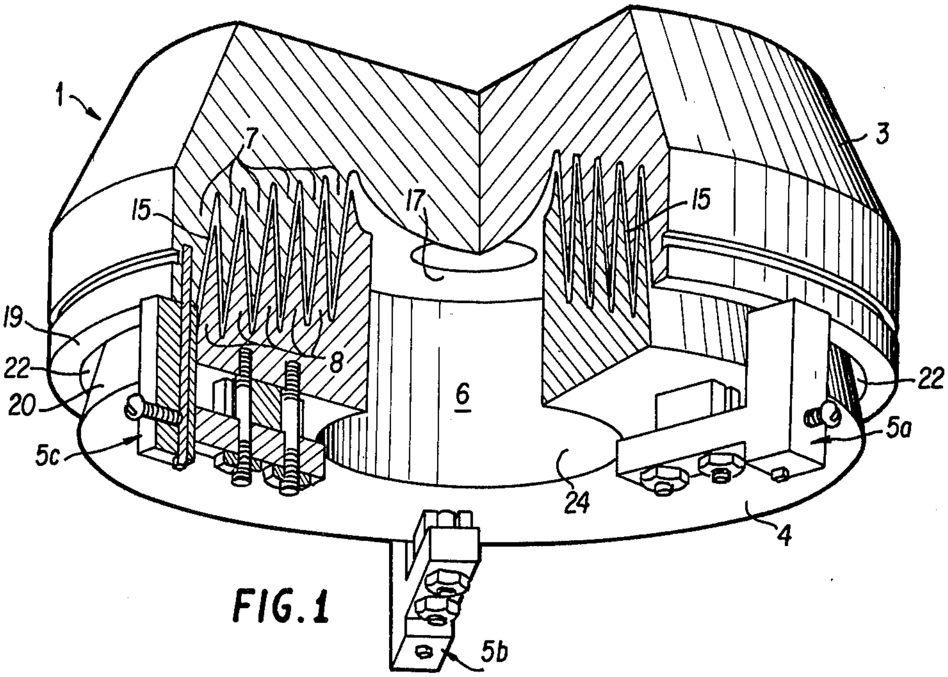
FIG. 1 is a perspective, partial cross sectional view of one of the preferred embodiments of the invention.
Figure 2:
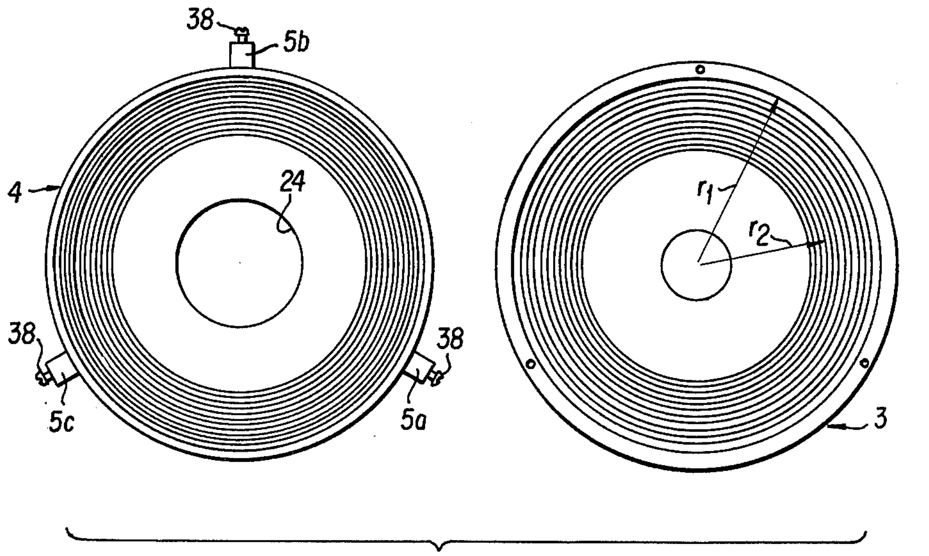
FIG. 2 is a plan, elevational view of the bottom surface of the top fractionating member and the top surface of the bottom fractionating member, illustrating the set of concentric corrugations in each.
Figure 3:
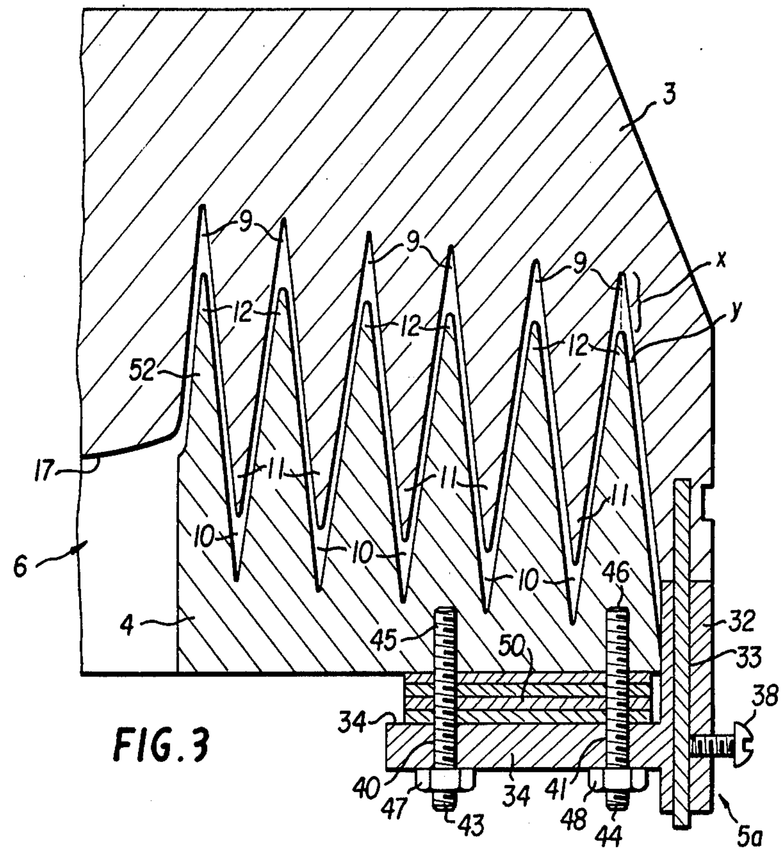
FIG. 3 is a partial cross sectional view of one preferred embodiment of the invention.

With reference to FIGS. 1, 2 and 3, the particle collection and fractionating apparatus of the invention 1 generally comprises a top fractionating member 3, a bottom fractionating member 4, and at least one spacer bracket 5*a*.

Top fractionating member 3 includes a plurality of concentric corrugations 7 and an annular edge portion 19 which circumscribes these corrugations 7. Each of the annular corrugations 7 includes a tapered peak portion 11, which widens down into two adjacent valley portions 9 as shown. As each of the corrugations 7 forms a particle collection and fractionating stage (as will become more apparent hereafter), top fractionating member 3 preferably includes at least six such corrugations 7 in order to effectuate thorough particle collection and fractionation. Top fractionating member 3 is preferably about six inches in diameter, although it should be noted that the exact dimensions of top fractionating member 3 are not at all critical to the proper operation of the apparatus of the invention. Finally, top fractionating member 3 includes a circular wall portion 17.

Bottom fractionating member 4 includes a plurality of concentric corrugations 8 which are complementary in shape to the concentric corrugations 7 of top fractionating member 3. Like the corrugations 7 of bottom fractionating member 4, each of the corrugations 8 of top fractionating member 4 includes a tapered peak portion 12 which widens into a pair of adjacent valley portions 10 as shown in the illustrations. The corrugations 8 are circumscribed by an edge portion 20, defined by the edge of bottom fractionating member 4. In the preferred embodiment, this edge portion 20 is actually the lip of a frustroconical skirt which defines the periphery of bottom fractionating member 4.

Bottom fractionating member 4 further includes a gas withdrawal means 6 including a port 24 for withdrawing a particle laden gas out from the center of the particle collector and fractionator 1. Gas withdrawal means 6 may include a source of negative pressure (not shown) such as a vacuum pump fluidly connected to port 24 for forcefully withdrawing a particle laden gas through the particle collector and fractionator and out the gas withdrawal means 6 located in the center of the invention 1. The invention 1 also contemplates the use of a particle filter (not shown) disposed in the fluid connection between the port 24 and the source of negative pressure for filtering out particles which are not collected by the collection and fractionating stages formed by the corrugations 7, 8 of the invention 1.

Figure 4:
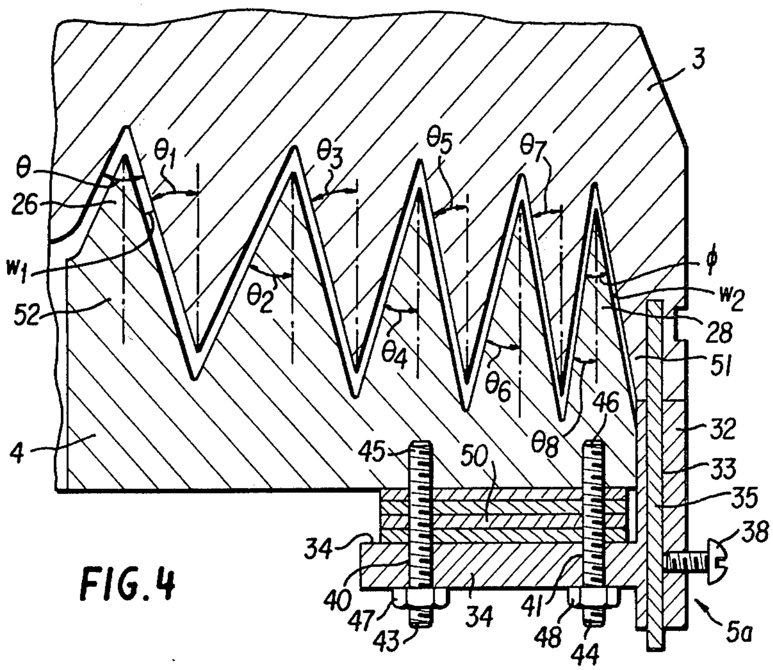
FIG. 4 is a partial cross sectional view of another preferred embodiment of the invention.

With reference now to FIGS. 1, 3 and 4, the preferred embodiment of the invention further includes three spacer brackets 5*a*, 5*b*, 5*c*, for spacing the concentric corrugations 7 of the top fractionating member 3 over the concentric corrugations 8 of the bottom fractionating member 4 in complementary relationship, as shown, with the peak portions 11 of the top fractionating member 3 interdigitating with the valley portions 10 of the bottom fractionating member 4 (and vice versa), as shown. Because of the complementary geometrical relationship between the corrugations 7 of top fractionating member 3 and the corrugations 8 of bottom fractionating member 4, it should be noted that bottom fractionating member 4 may be expeditiously fabricated from any one of a variety of moldable epoxy resins using the top fractionating member 3 as a mold.

When the top and bottom fractionating members 3, 4 are spaced together in a complementary relationship by means of spacer brackets 5*a*, 5*b*, 5*c*, a concentrically corrugated gas flow path 15 is defined therebetween. Furthermore, (and with particular reference to FIG. 1), an omnidirectional, 360 degree gas slit 22 which leads directly into the gas flow path 15 is formed by the edge portions 19, 20 of the top and bottom fractionating members 3, 4 respectively. Finally, when the invention is vertically oriented as shown in FIG. 1, that gas enters the 360 degree gas slit 22 at a narrow angle (less than 15°) from the vertical axis of the device, or about the same angle that air enters the nose of a human being standing or sitting erect.

With reference to FIGS. 1 and 3, the spacer brackets 5*a*, 5*b*, 5*c* each include an orthogonal member 31 having a vertical portion 32 and a horizontal portion 34. The vertical portion 32 includes a bore 33 for receiving a mounting rod 35, which is secured into top fractionating member 3 along its uppermost portion 36. Rod 35 is secured into bore 33 by means of a single mounting screw 38. The use of a single mounting screw 38 in each of the spacer brackets 5*a*, 5*b*, 5*c* allows the top and bottom fractionating members to be easily detached from one another when it is necessary to clean the invention 1. The horizontal portion 34 of orthogonal member 31 includes a pair of bores 40, 41 for receiving threaded studs 43, 44 which are threadedly engaged to bottom fractionating member 4 at their upper ends 45, 46 respectively. Horizontal portion 34 is in turn attached to the threaded studs 43, 44 by means of a pair of nuts 47, 48 in a conventional fashion. One or more shims 50 are interposed between the upper surface of horizontal portion 34 of orthogonal member 31 and the lower surface of bottom fractionating member 4 as shown. The number and width of these shims 50 may be adjusted to vary the width of gas flow path 15.

The accuracy of the flow path width control afforded by spacer brackets 5*a*, 5*b*, 5*c* is enhanced when the angles of the valleys 9, 10 and peaks 11, 12 of the corrugations 7, 8 are under 40°. This fact is best illustrated by FIG. 4. Here, the angle theta of the peak 26 of the centermost corrugation is much larger than the angle phi of the peak 28 of the outermost corrugation. It is apparent from this figure that as the bottom fractionating member 4 is lowered with respect to the top fractionating member 3, the width w1 in that segment of the gas flow path defined in part by peak 26 will grow much faster than the width w2 of that segment of the gas flow path 15 defined in part by the peak 28 of the outermost corrugation. Stated in more precise terms, since the rate of change of the width w1 of slit 15 is proportional to the cosine of one-half of the angle theta, the smaller theta is, the slower width w1 will change as top fractionating member 3 is vertically raised from bottom fractionating member 4. Thus relatively small peak and valley angles are preferable to large peak and valley angles simply because the rate of change of the width of the gas flow path 15 is much slower in the case of small peak and valley angles, which in turn enhances the accuracy of the gas flow width control afforded by spacer brackets 5*a*, 5*b*, and 5*c*.

In operation, particle laden gas enters the particle collector and fractionator 1 from any point along the 360 degree gas slit 22, where it is drawn through the concentrically corrugated gas flow path 15 toward the port 24 of the gas withdrawal means 6. As the particle laden gas travels radially through the zig zag cross section of the concentrically corrugated gas flow path 15, the particles are forced to make hairpin turns between each of the valley portions 9, 10 and the peak portions 12, 11 of the top and bottom fractionating members 3, 4. Additionally, the particles are made to slot down at these valley portions 9, 10 due to the fact that the cross section of gas flow path 15 widens at each of these valley portions. This difference in flow path widths is clearly illustrated in FIG. 3, where distance "x" represents the width of flow path 15 at the valley portions 9, 10 of the corrugations 7, 8 and distance "y" represents the width of the flow path 15 at all other points. The centripetal force associated with the hairpin turns, along with the lower gas stream velocity associated with the wider flow path at point x causes many of the particles to impact and collect in the valley portions 9, 10 of the corrugations 7, 8 of the top and bottom fractionating members 3, 4. When the top and bottom fractionating members 3, 4 are approximately 6 inches in diameter, the invention is capable of collecting and fractionating approximately one gram of such particles.

Assuming that gas withdrawal means 6 is fluidly connected to a source of negative pressure having a constant value over time, adjusting the relative height of the top fractionating member 3 over the bottom fractionating member 4 will in turn vary the width of the gas flow path 15 which will increase or decrease the velocity of a stream of particle laden gas flowing to centrally located port 24 from 360 degree gas slit 22 via gas flow path 15. Such variations in gas stream velocity will in turn determine the minimum aerodynamic size of the particles collected and fractionated in valley portions 9, 10 of the fractionating members 3, 4. As used in this specification, the term "aerodynamic size" refers to the diameter of a sphere of unit density which has the same terminal velocity as the particle in question in an identical carrying gas.

FIGS. 3 and 4 illustrate two different embodiments of the invention.

The particle collecting and fractionating apparatus of FIG. 3 is designed to collect and fractionate particles of progressively smaller aerodynamic sizes in the valley portions 9, 10 from the outermost corrugation 51 to the centermost corrugation 52. It does so because the annular cross sectional area of the gas flow path 15 gets progressively smaller as the stream of particle laden gas travels radially from the 360 degree gas slit 22 toward the center of the particle collector and fractionator 1. This is not immediately apparent from FIG. 3, because the cross sectional *width* of the gas flow path 15 between adjacent surfaces of corrugations 7, 8 is constant from the outermost corrugation 51 to the centermost corrugation 52. However, as clearly illustrated in FIG. 2, it must be noted that the gas flow path 15 is in reality a concentrically corrugated disc which follows the contours of the concentric corrugation 7, 8. Since the radius r2 of the centermost corrugation 52 is smaller than the radius r1 corresponding to the outermost corrugation 51, the total annular cross sectional *area* of gas flow path 15 is smaller around radius r2 than radius r1. Thus the velocity of a stream of gas flowing into the 360 degree gas slit 22 becomes correspondingly greater from a radial distance of r1 to a radial distance of r2.

A simple mechanical analogy will help clarify this concept. If we should suspend one hollow cone over another hollow cone of the same taper such that a cone shaped space of uniform thickness were formed therebetween, we would have a structure similar to the gas flow path 15 of the invention only without the hairpin turns formed by the corrugations 7, 8 of the top and bottom fractionating members 3, 4. Although the thickness of the space between the two cones remains uniform from the base of the cones to the tips, the annular cross sectional area of this space diminishes as we move toward the ends of the cones. Thus, if we should pump a gas through the slit formed around the concentric bases of the cones, it is readily apparent that the velocity of the gas would increase as it approached the tapered end of the cones.

In contrast to the embodiment illustrated in FIG. 3, the particle collecting and fractionating apparatus illustrated in FIG. 4 is designed to collect particles of approximately the *same* minimum aerodynamic size in each of the valley portions 9, 10 of corrugations 7, 8 of the top and bottom fractionating members 3, 4. This capacity is accomplished by enlarging the angles of the peak and valley portions 9, 10, 11, 12 of the corrugations 7, 8 from the outermost corrugation 51 to the centermost corrugation 52 such that the annular cross sectional area of gas flow path 15 remains constant between any two adjacent surfaces of corrugations 7, 8 at each point along radius r1. This in turn causes the velocity of the gas stream entering the invention 1 to remain substantially constant at all points along radius r1. For example, in the embodiment illustrated in FIG. 4, the velocity of a gas stream flowing radially through gas flow path 15 remains substantially constant if theta 1=20°, theta 2=18°, theta 3=12°, theta 4=10°, theta 5=9°, theta 6=8°, theta 7=7°, and theta 8=6.5°.

The constant cross sectional area of gas flow path 15 may again be analogized to the space between two hollow cones when one is suspended over the other. If the top cone has a longer taper than the bottom cone, the thickness of the cone-shaped space between them increases from the base to the tapered end of the cones. When the taper of the top cone is chosen such that the annular cross sectional area of the cone shaped space remains constant from the base to the point of the cones despite the decreasing conical radius, the cone shaped space is mechanically equivalent to gas flow path 15 except for the fact that it has none of the hairpin turns created by the peak and valley portions 9, 10, 11, 12 of the corrugations 7, 8.

It should be noted that, in both embodiments, the adjustable spacer brackets 5*a*, 5*b*, 5*c* serve to simultaneously adjust the minimum aerodynamic particle size collected at each of the fractionating stages defined by the valley portions 9, 10 of the corrugations 7, 8. Further, it will also be apparent to any person of ordinary skill in the art that the particle collection and fractionator of the invention will work equally well if the stream of particle laden gas enters port 24 and exits 360° gas slit 22. Finally, it is likewise apparent that the invention could work equally well in conjunction with a source of negative or positive pressure at either port 24 or slit 22.

Thus a particle collecting and fractionating device which is simple in construction and easy to clean and use has been described in such clear and concise terms so as to enable anyone of ordinary skill in the art to make and use the same.

In considering the invention, it will be understood that the invention is not limited to the particular embodiments described in detail above, or to any particular number of stages or materials, but only by the following set of claim definitions.

I claim:

1. A particle collector and fractionator, comprising (a) a bottom fractionating member having a plurality of concentric corrugations circumscribed by an edge portion, (b) a top fractionating member having a plurality of concentric corrugations which are complementary to the concentric corrugations of said bottom fractionating member, and which are likewise circumscribed by an edge portion, (c) at least one spacer bracket for spacing the corrugations of said top fractionating member over the corrugations of said bottom fractionating members in complementary relationship and forming an annular, concentrically corrugated gas flow path between said members which is circumscribed by a 360° gas slit defined between said edge portions of said fractionating members, and (d) means for withdrawing particle laden gas from the center of said annular, concentrically corrugated flow path, whereby particles in a stream of particle laden gas flowing into said flow path from said 360° gas slit and out through said gas withdrawal means are collected in each of the valley portions of said corrugations of said fractionating members.

2. The particle collector and fractionator of claim 1 wherein said gas withdrawing means includes a gas port disposed in the center of the concentric corrugations of said bottom fractionating member.

3. The particle collector and fractionator of claim 1 wherein said gas withdrawing means includes a port disposed in the center of the concentric corrugations of said top fractionating member.

4. The particle collector and fractionator of claim 2 or 3 wherein said gas withdrawing means further includes a source of constant negative pressure fluidly connected to said port.

5. The particle collector and fractionator of claim 4 wherein the annular cross sectional area of said gas flow path between each of the complementary concentric corrugations of said bottom and top fractionating members is substantially equal at any point along the radius of said concentric corrugations, whereby the minimum aerodynamic size of the particles fractionated in each of the valley portions of the corrugations is substantially equal.

6. The particle collector and fractionator of claim 5 wherein the annular cross sectional area of said gas flow path between the complementary concentric corrugations of said bottom and top fractionating members becomes successively smaller along the radius of said concentric corrugations from the outermost to the centermost corrugation, whereby the minimum aerodynamic size of the particles fractionated in each of the valley portions of the corrugations becomes successively smaller from the outermost to the centermost corrugation.

7. The particle collector and fractionator of claim 5 wherein said spacer bracket is adjustable for adjusting the annular cross sectional area of said gas flow path between said complementary concentric corrugations of said bottom and top fractionating members, whereby the minimum aerodynamic size of the particles fractionated in each of the valley portions of the corrugations may be selected by adjusting said bracket.

8. The particle collector and fractionator of claim 6 wherein said spacer bracket is adjustable for simultaneously adjusting all of said annular cross sectional areas of said gas flow path between said complementary concentric corrugations of said bottom and top fractionating members, whereby the range of minimum aerodynamic sizes of particles fractionated in each of the valley portions of the corrugations may be selected by adjusting said bracket.

9. The particle collector and fractionator of claim 7 wherein said top and bottom members each include at least six corrugations.

10. The particle collector and fractionator of claim 8 wherein said top and bottom members each include at least six corrugations.

11. The particle collector and fractionator of claim 9 wherein each of said edge portions forming said 360° gas slit are oriented at less than a 20° angle to the center axis of said concentric corrugations of said top and bottom fractionating member.

12. The particle collector and fractionator of claim 10 wherein each of said edge portions forming said 360° gas slit are oriented at less than a 20° angle to the center axis of said concentric corrugations of said top and bottom fractionating member.

* * * * *